(12) United States Patent
Van Den Broecke et al.

(10) Patent No.: US 7,309,599 B2
(45) Date of Patent: Dec. 18, 2007

(54) AEROBIC FERMENTATION METHOD

(75) Inventors: Pieter Marinus Van Den Broecke, SV Nootdorp (NL); Deodorus Jacobus Groen, CV Brielle (NL); Hendrik Jan Noorman, CA Delft (NL)

(73) Assignee: DSM IP Assets B.V., TE Heerlen (NL)

( * ) Notice: Subject to any disclaimer, the term of this patent is extended or adjusted under 35 U.S.C. 154(b) by 383 days.

(21) Appl. No.: 10/399,557

(22) PCT Filed: Sep. 26, 2001

(86) PCT No.: PCT/EP01/11320

§ 371 (c)(1),
(2), (4) Date: Apr. 18, 2003

(87) PCT Pub. No.: WO02/33048

PCT Pub. Date: Apr. 25, 2002

(65) Prior Publication Data

US 2004/0023359 A1   Feb. 5, 2004

(30) Foreign Application Priority Data

Oct. 19, 2000   (EP) ................... 00203663

(51) Int. Cl.
*C12N 1/20* (2006.01)
*C12N 1/14* (2006.01)
*C12N 1/18* (2006.01)
*C12N 1/16* (2006.01)

(52) U.S. Cl. .............. 435/252.1; 435/252.35; 435/252.8; 435/254.21; 435/254.1; 435/254.3

(58) Field of Classification Search ............ 435/252.1, 435/254.2, 254.3, 252.35, 252.8, 254.21, 435/254.1
See application file for complete search history.

(56) References Cited

U.S. PATENT DOCUMENTS

| 4,256,839 A | * | 3/1981 | Solomons et al. ....... 435/295.1 |
| 5,798,254 A | * | 8/1998 | Cheng ..................... 435/243 |
| 5,985,652 A | * | 11/1999 | Cheng ................... 435/286.6 |

FOREIGN PATENT DOCUMENTS

| EP | 0222529 | 1/1992 |
| EP | 0341878 | 10/1993 |
| EP | 0477818 | 5/1995 |
| EP | 0847800 | 8/2001 |
| EP | 0829534 | 12/2001 |
| EP | 0901812 | 3/2003 |
| JP | 62-119690 | 5/1987 |
| JP | 63-283570 | 11/1988 |

* cited by examiner

*Primary Examiner*—Maryam Monshipouri
(74) *Attorney, Agent, or Firm*—Nixon & Vanderhye P.C.

(57) ABSTRACT

A method and apparatus for effectively aerating large-scale cultures of microorganisms is disclosed.

19 Claims, 2 Drawing Sheets

AEROBIC FERMENTATION METHOD

CROSS-REFERENCE TO RELATED APPLICATION

Figure 1:
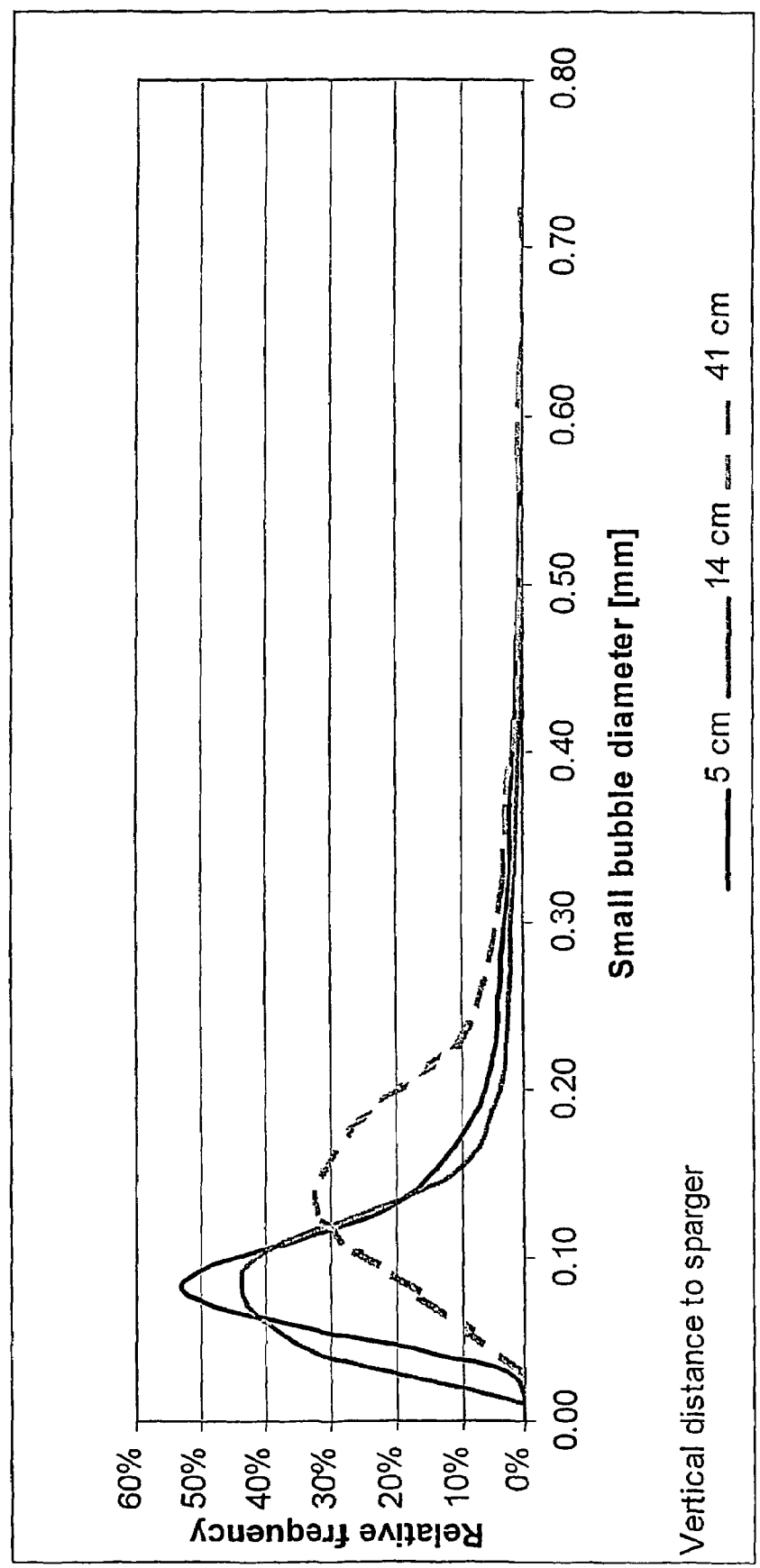

This application is the national phase of PCT application PCT/EP01/11320 having an international filing date of 26 Sep. 2001, and claims priority from European application Nr. 00203663.0 filed 19 Oct. 2000. The contents of these documents are incorporated herein by reference.

The present invention relates to a method of culturing a micro-organism under aerobic conditions in a fermentation vessel.

Industrial scale fermentation processes are carried out for the production of various products such as biomass (e.g. baker's yeast), enzymes, amino acids and secondary metabolites (e.g. antibiotics). Most of these fermentation processes involve the culturing of micro-organisms including bacteria, yeasts and fungi and require the supply of oxygen for the aerobic metabolism of these micro-organisms. Usually, the oxygen is supplied by passing an oxygen-containing gas, such as air, through the liquid in the fermentation vessel. The oxygen is transferred from the gas bubbles to the liquid phase thus allowing its uptake by the micro-organism. In fermentation processes involving large vessel volumes and high biomass densities, the transfer of oxygen from the gas to the liquid phase may become the growth limiting factor. Obtaining increased oxygen transfer is therefore one of the targets to obtain increased growth thus making these processes more economically attractive. Alternatively, fermentation processes that require for instance the carbon- or nitrogen source as the limiting factor in order to promote production of a certain product, require a non-growth limiting oxygen transfer rate. Hereto, processes have been developed that increase the oxygen transfer rate. Methods that are known in the art for increasing the oxygen transfer rate comprise: increasing the mixing (e.g. stirring) of the liquid, increasing the flow of oxygen-containing gas and/or increasing the oxygen concentration of the oxygen-containing gas (e.g. oxygen enriched air). Other methods are described that focus on the supply of two separate oxygen-containing gas streams.

European Patent Application EP-A-0,222,529 discloses the principle of improved oxygen enrichment of a fermentation broth by using a second oxygen-containing gas stream. The fermenting system consists of a vessel equipped with a riser and a downcorner; air is supplied to the broth in the riser, while in the downcorner a second oxygen containing gas is supplied to the broth. In the Japanese patent application JP-63-283570 this and other fermenting systems are disclosed that are equipped with means to circulate the flow, such as a draft tube or a (set of) impeller(s), an air stream for the purpose of circulation and $CO_2$ stripping and an oxygen supplying device that supplies oxygen in the direction that is opposite to the stream of the circulating fluid. The disadvantage of such a system is that the flow of the liquid inside the vessel must be known and sufficiently stable and controlled accurately in order to place the oxygen supplying device in such a way that the desired oxygen transfer is obtained. European Patent Application EP-A-0,341,878 discloses that the second oxygen containing gas may be supplied to the broth in a circulation loop outside the fermenter.

European Patent Application EP-A-0477818 discloses a similar method involving the injection of a feed air stream into a mixing vessel provided with impeller means having a vertical axis and separately injecting additional oxygen from an additional oxygen injection point. However, this method is limited by the fact that the latter injection point must be located remote from the vicinity of the air injection point in order to minimize mixing of the additional oxygen with the air bubbles.

In European Patent Application EP-A-0829534, the same principle is applied to a gas driven fermentation system, i.e. a system without mechanical mixing devices. The system employs injecting a first oxygen containing gas, such as air, in a set of bubbles upwardly through a vessel in a heterogeneous flow causing an upward flow of the broth in the vessel. The second oxygen-containing gas that is injected in the lower portion of the vessel is a set of bubbles also moving upwardly through said vessel in a homogeneous flow. The homogeneous flow is defined by the inventors as that the flow has a uniform gas bubble distribution and a narrow bubble size distribution wherein there is no observable gas/liquid downflow. The homogeneous character of this second gas is stated to be an essential feature. In contrast to the disclosure of JP-62-119690, the second oxygen-containing gas is not provided into the broth within the fermentor vessel at a region where the broth is flowing downwardly, rather, it must be provided into the broth where it is rising.

In European Patent Application EP-A-0,901,812 the method is further improved by providing oxygen directly into a 'stationary vortex', a rotating body of liquid with little or no axial or transverse movements supposedly created by a mechanical agitation system. The advantage is said to maintain the oxygen bubbles within the vortex until the oxygen bubble have dissolved into the reaction mixture. However, in industrial vessels it will be very difficult to locate the precise position of these stationary regions. Moreover, in highly turbulent gas-liquid mixtures as often applied in industry, it is likely that the vortices are not at all stationary.

FIG. 1. Small bubble size distribution for different distances from the sparger.

Figure 2:
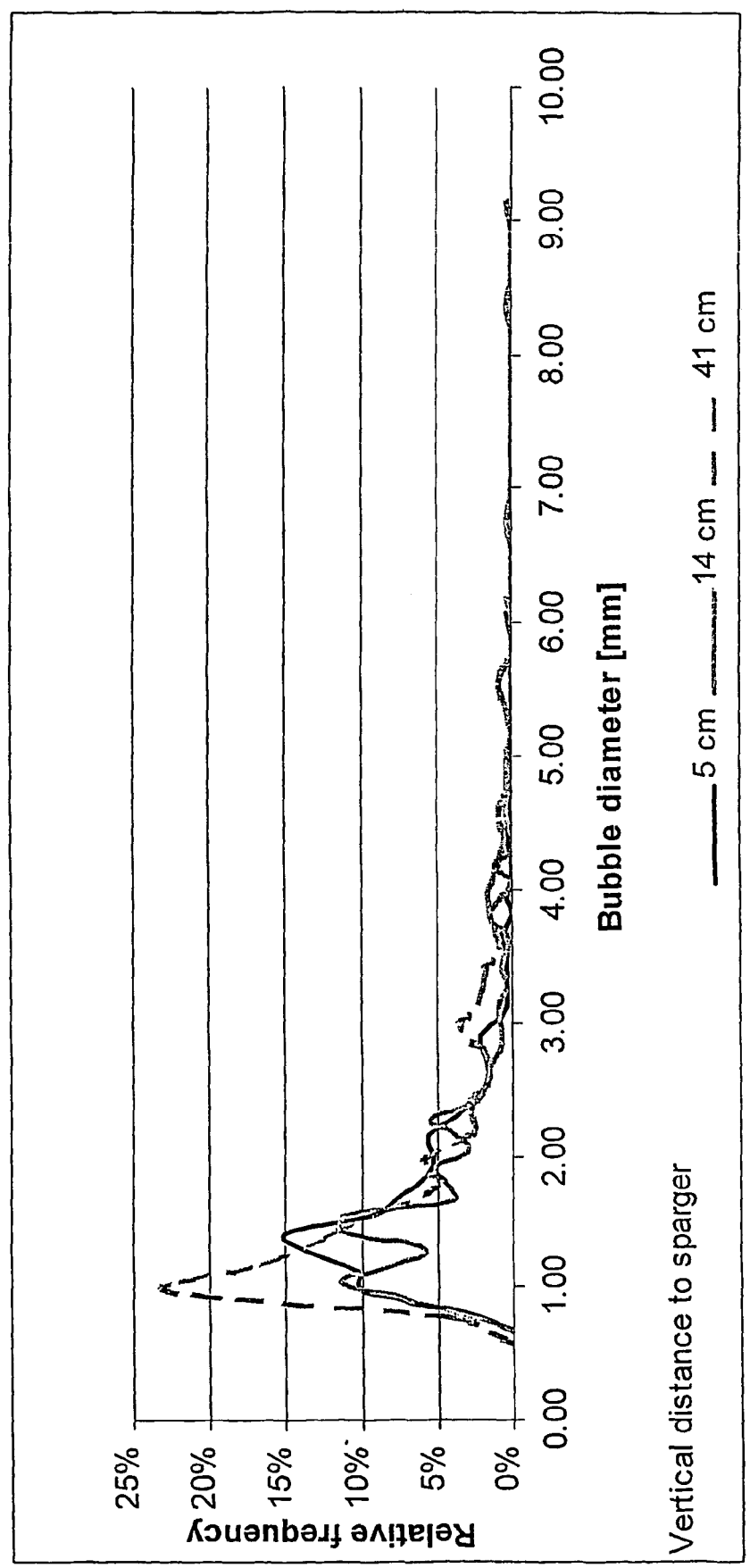

FIG. 2. Large bubble size distribution for different distances from the sparger

A homogeneous flow is defined herein as a flow in which all bubbles rise with the same velocity and the mixture follows straight streamlines with the absence of recirculatory liquid flows. Homogeneous flow can occur only when sparger holes are evenly distributed at the bottom of the vessel, and at superficial gas velocities<approx. 0.04 m/s.

A heterogeneous flow is defined herein as a flow in which local differences in liquid velocity will occur with the presence of recirculatory liquid flows. Heterogeneous flow will occur when sparger holes are unevenly distributed at the bottom of the vessel, or, at superficial gas velocities>approx. 0.04 m/s when sparger holes are evenly distributed.

Chaotic motion of the broth is defined herein as a movement, characterised by a direction and a velocity, which has a dependence on its history and conditions in the vessel and which is bound by certain limits (e.g. velocities can never exceed a certain maximum). This is different from random motion, which is a statistical quantity which has no dependence on the history, and is not bound by limits (e.g. extremely high velocities can occur, though with extremely low chance)

Turbulent flow is defined herein as liquid movement in which the momentum differences of individual liquid elements cannot be damped out by the viscosity of the liquid. As a result, circulating eddies will be formed in which liquid velocity differences will become more intense, with vigorous motion of the liquid.

A uniform size distribution of gas bubbles is defined herein as being a symmetrical distribution with a single maximum.

A non-uniform size distribution of gas bubbles is defined herein as a non-symmetrical distribution (e.g. with a tail to one side) or a distribution with more than one maximum.

A narrow size distribution of gas bubbles is defined herein as a distribution in which >95% of the bubbles have a diameter falling within the interval between $0.2*\emptyset_b$ and $5*\emptyset_b$, where $\emptyset_b$ is the average bubble diameter.

A wide size distribution of gas bubbles is defined herein as a distribution in which >95% of the bubbles have a diameter falling within the interval between $0.01*\emptyset_b$ and $100*\emptyset_b$, where $\emptyset_b$ is the average bubble diameter.

The present invention provides a method of culturing a micro-organism under aerobic conditions in a fermentation vessel comprising the injection of a first oxygen-containing gas into the lower portion of the vessel in a heterogeneous flow causing a chaotic motion of the broth and the introduction of a second oxygen-containing gas in the vessel characterised in that the second oxygen-containing gas is introduced as a heterogeneous flow of gas bubbles in the vessel in all possible directions and independent of the direction of the flow of the broth resulting in turbulent flow-conditions at the site of injection and as a set of gas bubbles of non-uniform size and a wide size distribution. The first oxygen-containing gas may contain from 15-30% oxygen (v/v), preferably from 20-30% oxygen and most preferably is air. The first oxygen-containing gas is injected into the lower portion of the fermentation vessel, preferably near the bottom. The second oxygen-containing gas may contain from 30-100% oxygen, preferably from 70-100% oxygen and most preferably is from 90-100% oxygen. The injection point of the second oxygen-containing gas is not limited to a certain area of the fermentation vessel and can be both in the vicinity or remote from the injection point of the first oxygen-containing gas, irrespective of whether the fermentation vessel is equipped with a mechanical stirring device or not. The advantage of the method of the present invention is that the oxygen transfer obtained by this method is improved over the existing methods of the prior art and does not put any limitations to the inlet position of the second oxygen-containing gas stream, thus allowing more flexibility in the fermentation vessel design. The method of the present invention is suitable for culturing yeasts, fungi and bacteria. Preferred examples of yeasts are members of the genera *Saccharomyces* or *Kluyveromyces* such as *Saccharomyces cerevisiae* and *Kluyveromyces lactis*. Preferred examples of fungi are members of secondary metabolite producing genera such as *Penicillium* (e.g. *Penicillium chrysogenum* for the production of penicillin and other antibiotics) and *Acremonium* and members of enzyme producing genera such as *Aspergillus* and *Trichoderma*. Preferred examples of bacteria are members of the genera *Streptomyces, Escherichia, Pseudomonas* or *Bacillus*.

One preferred embodiment is a method for culturing a micro-organism under aerobic conditions in a fermentation vessel wherein the broth is mixed by mechanical stirring. In another preferred embodiment, no mechanical stirring is applied but mixing of the broth is obtained by the first oxygen-containing gas stream such as air, i.e. the bell column fermenter.

The second-oxygen containing gas can be introduced in the fermentation vessel by means of simple pipes or gas spargers, orifices, venturi type nozzles, gas-liquid nozzles or supersonic gas injection nozzles. Preferably, the second-oxygen containing gas is introduced by one or more nozzles each comprising at least one hole. More preferably, the second-oxygen containing gas is injected in the fermentation vessel in three dimensions. This can be obtained by using several nozzles each comprising at least one hole which nozzles are positioned in the fermenter in a suitable arrangement to give injection in three dimensions. Alternatively, one or more nozzles may be used each containing at least 3 holes arranged such to give injection in three dimensions.

EXAMPLE 1

Air was sparged through a nozzle fitted in the vicinity of the bottom of a glass tank (0.6 m diameter) filled with 300 liter of a 4% $Na_2SO_4$ solution in water. The $Na_2SO_4$-solution was used to mimic the coalescence properties of a fermentation broth and to provide the transparency needed for the detection techniques that were used. The nozzle contained 7 holes of 1 mm diameter, 6 of which were equally spaced in a circle of 32 mm diameter and one positioned in the center. The nozzle flow was directed upward. Gas hold-up and bubble size distribution were measured in the gas plume at various vertical positions above the sparger. The gas hold-up was measured with a radioactive transmission technique using a Cs137 gamma radiation source and a NaI detector. This technique measures the total density of the gas-liquid mixture in the detection zone vessel and thus allows the calculation of the gas fraction. The bubble size distribution expressed as Sauter mean d32 was determined by image analysis of video recordings of optical magnifications of the bubble patterns (T. Martin—PhD thesis: Gas dispersion with radial and hydrofoil impellers in fluids with different coalescence characteristics. 1996. Herbert Utz Verlag, München (D)). Table 1 and FIGS. 1 and 2 show the results for a nozzle exit velocity of 490 m/s. A non-uniform bubble size distribution was observed with typical peaks in the small range between 0.2 and 0.3 mm (FIG. 1) and in the large diameter range between 2 and 4 mm (FIG. 2) with a typical holdup of 1.1% for the small bubbles and 1-3% for the large bubbles.

TABLE 1

| Vertical position (cm) | Gas hold-up | | Sauter d32 | |
| --- | --- | --- | --- | --- |
| | Small bubbles (%) | Larger bubbles (%) | Small bubbles (mm) | Larger bubbles (mm) |
| 5 | 1.1 | 0.1 | 0.267 | 2.273 |
| 14 | 1.1 | 1.3 | 0.216 | 2.630 |
| 41 | 1.1 | 2.2 | 0.287 | 3.587 |

EXAMPLE 2

*Saccharamyces cerevisiae* was cultured in a bubble column fermenter equipped with an air (i.e. the first oxygen containing gas) sparger near the bottom of the fermenter and a recirculation loop with an external heat-exchanger for cooling. Superficial air flow rates were approximately 0.20 m/s and the oxygen transfer was 0.4-0.6% per meter of the unaerated broth height. The broth was circulated through the heat exchanger four times per hour. Other fermentation conditions were as described by Reed, G and Nagodawithana, T. W. in chapter 6 of YEAST TECHNOLOGY (1991, Van Nostrand Reinhold, New York). The second oxygen containing gas consisted of pure oxygen and was injected below the air sparger, employing nozzles operated under a pressure of approximately 5 bar with hole diameters in the order of 1 mm, in order to achieve supersonic injection velocities of the oxygen, resulting in a non-uniform oxygen bubble distribution. We selected the inlet position below the oxygen sparger to allow the fraction of larger oxygen bubbles (50-70 vol %) to move upward and coalesce with the air bubbles and to allow the fraction of small bubbles to be entrained in the recirculation flow. In this way, optimum pressure and residence time conditions were created to achieve near total oxygen uptake (100% efficiency), whereas the fraction of large bubbles showed the transfer efficiency of the air flow. The ratio of the two gas flows (air/oxygen) was 9:1. Yeast productivity was approximately 8-9 kg biomass (dry wt) per kg broth per hour which is twice the productivity found without injection of the second oxygen-containing gas. The following results are depicted in Table 2.

TABLE 2

| $O_2$-containing gas | | $O_2$ Transfer Efficiency (%) | $O_2$ Transfer Rate (mmole $O_2$ per kg broth per hour) | Relative $O_2$-Transfer Rate (-fold) |
|---|---|---|---|---|
| $1^{st}$ | Air | 20 | 140 | 1 |
| $2^{nd}$ | Pure $O_2$ | | | |
| | large bubbles | 20 | 60 | |
| | small bubbles | 100 | 70 | |
| | Total: | | 270 | 1.9 |

EXAMPLE 3

A fermentation was carried out similar to the one described in Example 2 except that the ratio of the two gas flows (air/oxygen) was 6:1 and the yeast productivity was approximately 16 kg biomass (dry wt) per kg broth per hour. Table 3 gives the results.

TABLE 3

| $O_2$-containing gas | | $O_2$ Transfer Efficiency (%) | $O_2$ Transfer Rate (mmole $O_2$ per kg broth per hour) | Relative $O_2$-Transfer Rate (-fold) |
|---|---|---|---|---|
| $1^{st}$ | Air | 15 | 140 | 1 |
| $2^{nd}$ | Pure $O_2$ | | | |
| | large bubbles | 15 | 90 | |
| | small bubbles | 100 | 270 | |
| | Total: | | 500 | 3.6 |

Compared to Example 2, a further increase in the $O_2$-Transfer Rate was observed which is explained by the fact that a higher $O_2$ consumption occurred as a result of an increased productivity of the yeast.

EXAMPLE 4

*Saccharomyces cerevisiae* was grown in a stirred tank fermenter, equipped with an air sparger below the bottom impeller, and a second sparger which was placed in the radial liquid flow stream generated by the bottom impeller. The impeller was of the turbine disk type. The second sparger was equipped with nozzles of the type as described in example 2, and through this sparger a second oxygen containing gas was supplied, consisting of pure oxygen. The position of the second sparger was chosen to be located in the most vigorously agitated part of the liquid as to demonstrate that the positive effect of the generation of the oxygen bubbles is not limited to locations where the flow conditions are relatively stagnant.

In addition to a reference fermentation with only air, two experiments have been executed with extra oxygen. In one fermentation, the air stream was enriched by replacing approximately 6% of the air by pure oxygen. In the second fermentation, the same amount of oxygen was supplied by direct injection through the second sparger, while having the air flow in the first sparger reduced to 94%. The oxygen concentration in the liquid phase was controlled at 20% of air saturation. Results of the oxygen transfer rate at the end of the fermentation are shown in Table 4.

TABLE 4

| Experiment | $O_2$ transfer rate (mmole $O_2$ per kg broth per hour) |
|---|---|
| Reference | 35 |
| Enrichment | 44 |
| Direct injection | 50 |

The improvement of the oxygen transfer rate with the enriched air can be attributed to a higher driving force from gas to liquid phase. The measured magnitude is in agreement with the expectations.

The improvement with the direct injection experiment can be attributed to a cumulative contribution of transfer by the air from the air sparger, by a fraction of large oxygen bubbles from the second sparger and a fraction of small bubbles also from the second sparger. Assuming that the ratio of large to small oxygen bubbles is 5:1, then the contributions of air, large oxygen bubbles and small oxygen bubbles to the total-oxygen transfer rate is 34, 10 and 6 mmoles per kg broth per hour, respectively.

The invention claimed is:

1. A method of culturing a micro-organism which is a fungus or a bacterium under aerobic conditions in a fermentation vessel containing broth, said method comprising
   a) injecting a first oxygen-containing gas into the lower portion of the vessel in a heterogeneous flow causing a chaotic motion of the broth, and
   b) injecting a second oxygen-containing gas into the vessel as a heterogeneous flow of gas bubbles moving in the vessel in all possible directions, independent of the direction of the flow of the broth resulting in turbulent flow conditions at the site of said injection of said second gas;
wherein said gas bubbles are of wide non-uniform size distribution,
wherein steps a) and b) are performed simultaneously and continuously during said culturing.

2. The method according to claim 1, wherein the micro-organism is a yeast.

3. The method according to claim 2, wherein the micro-organism is a yeast belonging to the genus *Saccharomyces* or *Kluyveromyces*.

4. The method according to claim 3, wherein the yeast is *Kluyveromyces lactis*.

5. The method according to claim 1, wherein the micro-organism is a fungus belonging to the genus *Penicillium, Acremonium, Aspergillus* or *Trichoderma*.

6. The method according to claim 5, wherein the fungus is *Penicillium chrysogenurn*.

7. The method according to claim 1, wherein the micro-organism is a bacterium belonging to the genus *Streptomyces, Escherichia, Pseudomonas* or *Bacillus*.

8. The method according to claim 1, wherein the broth is mixed by mechanical stirring.

9. The method according to claim 1, wherein the second oxygen-containing gas is injected in the fermentation vessel by means of one or more nozzles each comprising at least one hole.

10. The method according to claim 9, wherein the nozzles are positioned in the fermentation vessel so as to obtain injection of the second oxygen-containing gas in three dimensions.

11. The method according to claim 9, wherein the holes are positioned in the nozzle so as to obtain injection of the second oxygen-containing gas in three dimensions.

12. The method of claim 1, wherein the first oxygen-containing gas and the second oxygen-containing gas are different.

13. The method of claim 12, wherein the second oxygen-containing gas contains more oxygen than the first oxygen-containing gas.

14. The method of claim 13, wherein the first oxygen-containing gas contains 15-30% oxygen (v/v) and the second oxygen-containing gas contains 30-100% oxygen (v/v).

15. The method of claim 14, wherein the first oxygen-containing gas contains 20-30% oxygen (v/v) and the second oxygen-containing gas contains 70-100% oxygen (v/v).

16. The method of claim 15, wherein the first oxygen-containing gas is air and the second oxygen-containing gas contains 90-100% oxygen (v/v).

17. A method of culturing a micro-organism which is a fungus or a bacterium under aerobic conditions in a fermentation vessel containing broth, said method comprising
   a) injecting a first gas containing 20-30% oxygen (v/v) into the lower portion of the vessel in a heterogeneous flow of bubbles to cause a chaotic motion of the broth and
   b) injecting a second gas containing 70-100% oxygen (v/v) into the vessel as a heterogeneous flow of bubbles moving in the vessel in all possible directions to cause turbulent flow of the broth, wherein bubbles of said second gas are of non-uniform size and wide size distribution;
wherein steps a) and b) are performed simultaneously and continuously during said culturing.

18. The method according to claim 17, wherein the micro-organism is *Saccharomyces cerevisiae*.

19. A method of culturing a micro-organism which is *Saccharomyces cerevisiae* under aerobic conditions in a fermentation vessel containing broth, said method comprising
   a) injecting a first oxygen-containing gas into the lower portion of the vessel in a heterogeneous flow causing a chaotic motion of the broth, and
   b) injecting a second oxygen-containing gas into the vessel as a heterogeneous flow of gas bubbles moving in the vessel in all possible directions, independent of the direction of the flow of the broth resulting in turbulent flow conditions at the site of said injection of said second gas;
wherein said gas bubbles are of wide non-uniform size distribution,
wherein steps a) and b) are performed simultaneously and continuously during said culturing.

* * * * *